Figure 1:
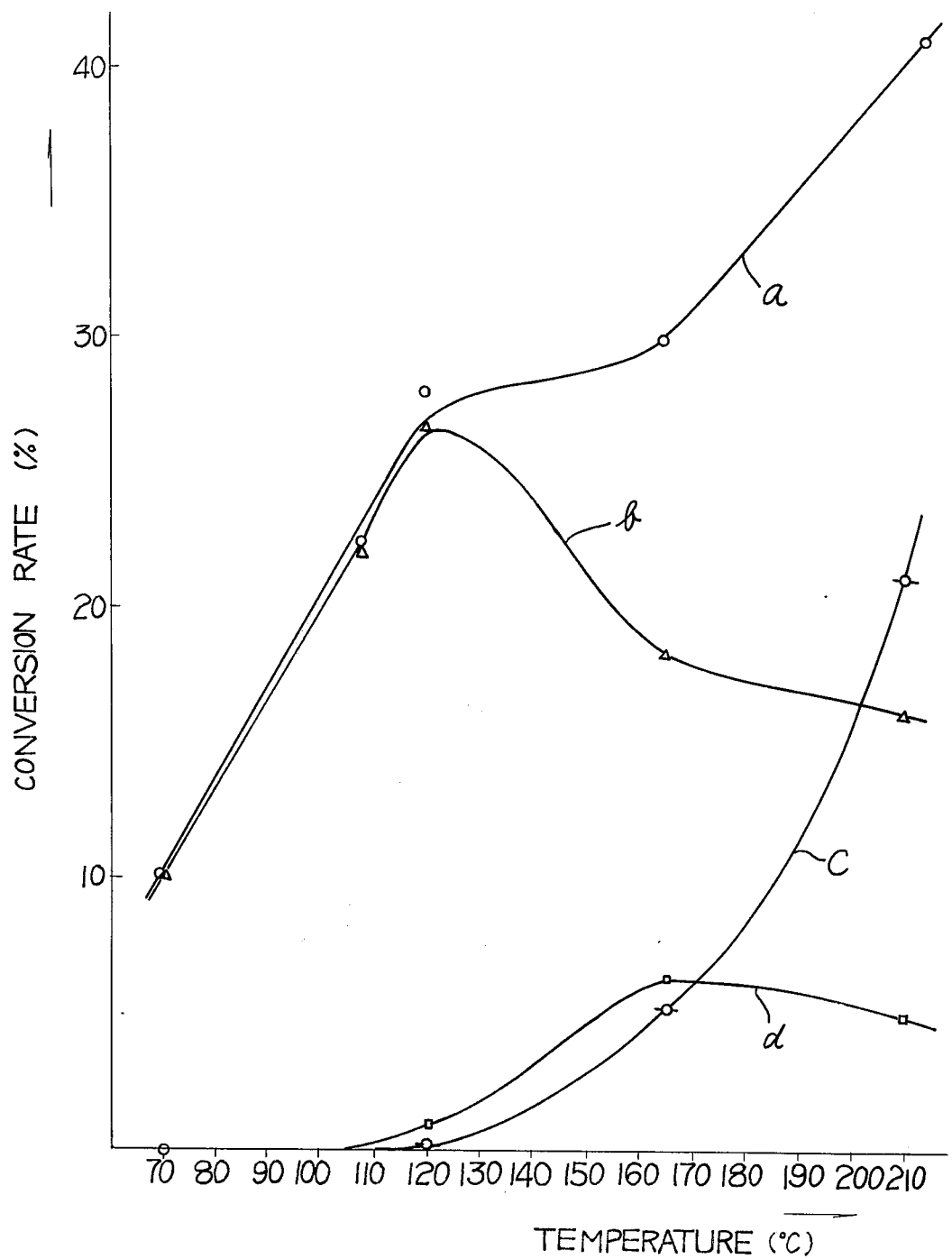

United States Patent [19]

Mizutani et al.

[11] 3,946,079
[45] Mar. 23, 1976

[54] METHOD OF CONDENSING KETONES
[75] Inventors: Yukio Mizutani, Tokuyama; Yusuke Izumi, Yamaguchi; Yoshiaki Watanabe, Hikari, all of Japan
[73] Assignee: Tokuyama Soda Kabushiki Kaisha, Japan
[22] Filed: Jan. 7, 1971
[21] Appl. No.: 104,735

Related U.S. Application Data
[63] Continuation of Ser. No. 780,622, Dec. 3, 1968, abandoned.

[30] Foreign Application Priority Data
June 24, 1966  Japan.................. 41-40653

[52] U.S. Cl.......... 260/593 R; 252/437; 260/590 D; 260/592; 260/586 R; 260/668 R
[51] Int. Cl.² ........................................ C07C 45/00
[58] Field of Search ........ 260/593 R, 586 R, 586 C, 260/590, 592, 668 R

[56] References Cited
UNITED STATES PATENTS

| | | | |
|---|---|---|---|
| 2,288,306 | 6/1942 | Wagner............................ | 260/593 R |
| 2,309,650 | 2/1943 | McAllister et al............. | 260/593 R |
| 3,098,100 | 7/1963 | Freure............................. | 260/593 R |
| 3,153,068 | 10/1964 | Porter et al........................ | 260/593 |

Primary Examiner—Bernard Helfin
Assistant Examiner—James H. Reamer
Attorney, Agent, or Firm—Sherman & Shalloway

[57] ABSTRACT

A process of producing ketone condensation products which comprises condensing at a temperature of from 60° to 300°C. a ketone having 3–19 carbon atoms in the presence of, as a catalyst, at least one metal phosphate selected from titanium phosphate, zirconium phosphate, hafnium phosphate, and tin phosphate; dimeric condensation or trimeric condensation can be achieved depending upon the reaction conditions.

4 Claims, 1 Drawing Figure

METHOD OF CONDENSING KETONES

This application is a continuation of Ser. No. 780,622 filed Dec. 3, 1968 now abandoned.

This invention relates to a method of condensing ketones using as catalyst the phosphates of the metals of group IV of the periodic system of elements.

More particularly, the invention relates to a method of condensing ketones which uses as catalyst at least one of the metal phosphates selected from the group consisting of zirconium phosphate, titanium phosphate, hafnium phosphate and tin phosphate.

The condensation method of the present invention can be applied widely to the ketones which are condensable.

The term "ketones" is a generic term of those organic compounds having the atomic group indicated by the formula

i.e. the carbonyl group. According to the present invention, it is possible (a) to effect the condensation reaction between ketone molecules in which at least one hydrogen atom is attached to either one or both of the two carbon atoms that are attached to the foregoing carbonyl (hereinafter referred to as the carbon atoms of the alpha position) and (b) to effect the condensation reaction between a ketone molecule in which two or more hydrogen atoms are attached to either one or both of the foregoing carbon atoms of the alpha position and a ketone molecule having no hydrogen atom whatsoever attached to these carbon atoms of the alpha position. Further, not only dimeric condensation but also condensation of trimeric or more is possible depending upon the class of ketones and the reaction conditions.

As a result of these condensation reactions of ketones it becomes possible by, say, the dimeric condensation reaction of acetone to produce mesityl oxide, the starting material in the production of methylisobutylketone which excels as a solvent.

A method of condensing the carbonyl compounds which uses as catalyst synthetic zeolite has been proposed heretofore. However, this method had various shortcomings such as the inadequacy of the yield of the condensation reaction, the greatness of the decline in activity of the catalyst and the difficulty of preparing the catalyst.

It is therefore an object of the present invention to provide a method by which the of dimers, trimers or higher condensation products of ketones can be obtained selectively and in good yield and economically advantageously. A further object is to provide a method whereby mesityl oxide can be obtained by the dimeric condensation of acetone. An additional object is to provide a new catalyst for use in condensing ketones. Still another object is to provide a method of preparing the new catalyst which demonstrates especially high activity in the condensation of ketones. Other objects and features of the present invention will become self-evident from the description which follows.

The catalyst to be used in the present invention is at least one of the metal phosphates selected from the group consisting of zirconium phosphate, titanium phosphate, hafnium phosphate and tin phosphate, which may be used as such or after being supported on an inert carrier such as diatomaceous earth, alumina, silica and clay. Further, the catalyst, as such, or supported on a carrier can be used in any of the forms of either powder or granular form.

The catalyst of the present invention is obtained by reacting phosphoric acid with one or more water-soluble salts of zirconium, titanium, hafnium or tin and isolating the precipitate which forms. The reaction of this invention is a reaction between the foregoing metals and the phosphate ion ($PO_4^{-3}$) in an aqueous medium, and hence the foregoing phosphoric acid need not be phosphoric acid itself but can be any salt of phosphoric acid, which can provide the phosphate ion ($PO_4^{-3}$). Particularly to be preferred are an acidic phosphate and phosphoric acid. In the present invention, these precipitates are referred to as, respectively, zirconium phosphate, titanium phosphate, hafnium phosphate and tin phosphate in correspondence to the metal component contained in the aforesaid water-soluble salt. The method of preparing these metal phosphates which make up the catalyst of the present invention is imposed no particular restriction, and any of the different methods which have been hitherto reported as being methods of manufacturing the inorganic ion-exchangers can be used without change. As an example, that according to J. Inorg. and Nucl. Chem. 6 220 (1958) is carried out in the following manner. 540 Milliliters of a solution of $H_3PO_4$ (54.2 grams/liter) are rapidly added with stirring to 556 ml of a ZrO($NO_3$)$_2$/1N-$HNO_3$ solution (107 grams ZrO($NO_3$)$_2$.2$H_2O$ per liter), followed by stirring for 10 – 15 minutes. The resulting gel-like precipitate is washed by adding a large quantity of distilled water followed by decantation. This washing operation is repeated several times until the pH of the filtrate become up to 3 to thereby eliminate the nitrate ion and excess of the acid. This is followed by collecting the product by vacuum filtration and drying of the product at about 30°C. to obtain zirconium phosphate.

The zirconium phosphate obtained as described above can be used as catalyst in the present invention, but it is to be understood that the method of preparing the catalyst is not restricted to that described. In a precipitate finely divided form obtained by the reaction of phosphoric acid with any water-soluble salt of at least one of the metals selected from the group consisting of zirconium, titanium, hafnium and tin can be used in the present invention as the catalyst.

However, (A) that obtained, when reacting the aforesaid water-soluble salt and the phosphoric acid, by using a mole ratio of the phosphate ions ($PO_4^{-3}$) to the foregoing metals (hereinafter indicated by Me), i.e., a mole ratio $PO_4^{-3}$/Me, of a range 0.6–1.7 to 1.0, and thereafter isolating the so obtained precipitate is desirably used as a catalyst. If in this case the foregoing precipitate is dried without heating, a catalyst having a particularly great specific surface area is obtained to become a catalyst having superior activity.

On the other hand, (B) a catalyst obtained by reacting the phosphate ions ($PO_4^{-3}$) with a water-soluble salt of at least one of the metals selected from the group consisting of zirconium, titanium, hafnium and tin, in an aqueous solution of pH of at least 3, and preferably not greater than 12, followed by drying the so formed gel-like precipitate also has an especially great specific surface area and is an excellent catalyst. While there is no especial restriction in this case as to the mole ratio of the phosphate ions ($PO_4^{-3}$) to the metal in the reaction system for preparing the catalyst and it is possible to use either one of the components greatly in excess, a convenient range from standpoint of economy is usually a range in which one of the components does not exceed threefold molar quantity of the other, because there is no particular technical advantage in using one of the components in excess of threefold molar quantity of the other.

As regards the method of adjusting the pH of the reaction system to between 3 and 12 in the catalyst preparation reacton of (B), above, preferred are the following methods:

i. The method of adding a strong alkali to the reaction system, such as caustic alkalis, caustic alkaline earth metals and alkali carbonates; and ii. The method of adding ammonia to the reaction system.

In the former case, i.e. the case of (i), the precipitate obtained by the catalyst preparation reaction has a tendency generally of being partly substituted by the foregoing strong alkalis. Hence, an acid treatment of the precipitate obtained must be carried out after the reaction to effect the substitution of hydrogen ions for the aforesaid strong alkali. On the other hand, in the latter case, i.e. the case of (ii), the phosphoric acid component is still maintained as an acidic phosphate even though the pH is raised to as high as about 12 and a part of the precipitate resulting from the reaction is partly substituted by ammonium ions. Hence, when the precipitate, after isolation from the reaction solution, is heated and dried at 300°–600°C., the ammonia is readily decomposed and eliminated to yield an excellent catalyst.

Thus, the phosphates of the foregoing metals, i.e. the catalyst of the present invention which has a great surface area (100–300 m²/gr. or more), can be obtained by the above-described catalyst preparation methods of the present invention.

The catalyst of the present invention, i.e. zirconium phosphate, titanium phosphate, hafnium phosphate or tin phosphate, prepared as hereinbefore described, is formed with differing structures depending upon the mole ratio of the phosphate ion ($PO_4^{-3}$) to the metal (Me), and it is further believed that the structure also varies depending upon such as the temperature at which the precipitate obtained by the aforesaid reaction is heated. However, those of any structure prepared by the hereinbefore described methods can be used as catalyst in the present invention.

Further, while the foregoing metal phosphates are all effective as catalysts in the present invention, there is some difference in catalytic activity depending upon the class of metal making up the catalyst, those of zirconium and titanium demonstrating the highest activity, next preferred being that of hafnium.

The catalyst used in this invention is featured first in that its activity is great even at relatively low temperatures. Particularly, the catalyst which has been prepared in accordance with the previously described methods can effect the condensation of the starting ketones at a conversion rate above 30 % even at temperatures of 70°–150°C. Secondly, the catalyst of the present invention possesses high activity. Hence, at particularly elevated temperatures of above 200°C. trimers of ketones can be obtained in good yield. For example, when acetone is used as the ketone, it is possible to obtain mesitylene at a selectivity exceeding 60 % by a suitable choice of the conditions. Thirdly, it is possible to produce the dimeric and trimeric condensation products at an optional ratio by controlling the reaction temperature.

No particular restrictions are imposed on the mode of the condensation reaction of ketones in the present invention. Hence, the vapor phase catalytic reaction in which the vapor of ketones is passed over the catalyst and the liquid phase catalytic reaction in which the ketones in liquid state are contacted with the catalyst can both be employed. Again, it is also possible to contact the ketones along with an inert diluent, if desired.

The condensation reaction of this invention is usually carried out in the temperature range of 60°–300°C. Even in this temperature range, there is a tendency to an increase in amounts of the trimeric condensation products and the overall amount converted, with the temperature getting higher.

There is no particular restriction as to the pressure during the reaction of the present invention, but similarly as in the case of the usual condensation reactions an improvement in the overall conversion rate is noted as the pressure becomes higher. However, in order to carry out the invention reaction in the liquid phase, the reaction must be carried out at a pressure which is higher than the vapor pressure, at the temperature at which the reaction is being carried out, of the ketone which is participating in the reaction. When the condensation reaction of the ketones is carried out in the liquid phase, the yield of the dimeric condensation products can be especially enhanced. On the other hand, when the condensation reaction of the ketones is to be carried out in the vapor phase, there is also no particular restriction as to the reaction pressure, but commercially a pressure of the order of normal atmospheric to 100 atmospheres is usually employed. Needless to say, a pressure exceeding 100 atmospheres can also be employed.

Therefore, when it is contemplated to cause the previously described dimerization of ketones to proceed mainly, it is preferred that the reaction be carried out at a temperature generally of 60°–160°C., and particularly 80°–130°C. Further, it is particularly preferred that the dimerization be carried out in the presence of the aforesaid catalyst while maintaining the ketone in the liquid phase.

On the other hand, when it is contemplated to obtain principally the trimeric condensation products of ketones by the invention method, the condensation reaction is preferably carried out at above 160°C., and particularly 200°–300°C. Further, it is an advantage to carry out this reaction at a temperature and pressure at which the ketones are maintained in their vapor phase.

The reaction apparatus to be used in the present invention is not particularly restricted, and the conventional reaction apparatus can be used without change. That is to say, either the batch or continuous type can be employed, and as to the continuous type either the fixed catalyst bed or fluidized catalyst bed type can be used. When it is especially desired to obtain the dimeric condensation products of ketones, the liquid phase continuous reaction type of apparatus is preferred. In this case, it is convenient since the durability of the catalyst activity is enhanced.

Thus, the invention method makes it possible to carry out a. the condensation reaction between ketone molecules in which at least one hydrogen atom is attached to either one or both of the carbon atoms of the alpha position that are attached to a carbonyl group; and
b. the condensation reaction between a ketone molecule in which at least two hydrogen atoms are attached to either one or both of the foregoing carbon atoms of alpha position and a ketone molecule having no hydrogen atom whatsoever attached to these carbon atoms of the alpha position.

As the ketones belonging to (a), above, any having the following structure will do:

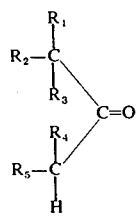

wherein $R_1$, $R_2$, $R_3$, $R_4$ and $R_5$, which are the same or different, are each hydrogen, alkyl, cycloalkyl, aryl, aralkyl, alkaryl or alkenyl; and conveniently used are ketones whose total of carbon atoms is 3–19. As described below, in additon to the ketones embraced by the above formula, acetophenone can be advantageously employed in accordance with the method of the present invention. According to the present invention, these ketones of the same or different class i.e., structural formula can be used to carry out the dimeric, trimeric or more polymeric condensation reaction. As in apparent from above the preferred ketones which can be condensed by the process of the present invention are those having a total of 3–19 carbon atoms having the formula

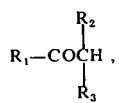

wherein $R_1$ is either alkyl, cycloalkyl, aryl, aralkyl, alkaryl or alkenyl and $R_2$ and $R_3$, which may be the same or different are each hydrogen alkyl, cycloalkyl, aryl aralkyl, alkaryl or alkenyl.

In the case of (b) above, the condensation reaction is carried out between a ketone belonging to (a) above in which at least either $R_4$ or $R_5$ is a hydrogen atom and a ketone which possesses no hydrogen atom at all in the alpha position, e.g. diphenylketone or di-tertiary butylketone. However, according to the present invention, the condensation reaction of those ketones belonging to (a) above, can be carried out especially conveniently.

Further, in order to obtain the ketone condensation products in good yield in this invention, it is preferred that a single class of ketone be condensed, i.e. the ketone is reacted with itself. When a mixture of different ketones is condensed, the formation of products of diverse structural formulas take place to make their separation complicated.

Ketones which are desirably condensed by the invention method include such, for example, as acetone, methyl ethyl ketone, diethylketone, methylpropylketone, methylisobutylketone, ethylhexylketone, dinonylketone, acetophenone, methylcyclohexylketone, isopropyl tert.butylketone and isopropylphenylketone.

According to this invention, the ketones such as indicated above can by a suitable choice of the reaction conditions be converted either to principally dimeric condensation products or to principally trimeric condensation products or to higher polymeric condensation products. Furthermore, the present invention makes it possible to carry out these condensation reaction of ketones at a very high rate of conversion and selectivity, as well as with ease as regards to operation of the reaction.

Thus, it is possible in accordance with the present invention to condense, say, acetone at a high rate of conversion and high selectivity to obtain its dimeric condensation product, mesityl oxide

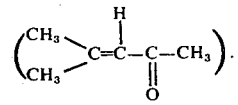

Next, by using as catalyst, say, metallic palladium or an inert carrier supporting the same and carrying out the catalytic hydrogenation, methylisobutylketone can be produced at a high rate of conversion.

The following examples are given for illustrating the invention more specifically, it being understood however that these examples are not intended to limit the present invention. Examples 1–8 illustrate different methods of preparing the catalysts which are usable in the present invention, whereas Example 9 et seq. illustrate instances of reactions in which the condensation of ketones has been carried out using the foregoing catalysts. The confirmation of the reaction products in Example 9 et seq. was conducted by means of chromatographic analysis.

EXAMPLE 1

One hundred and twenty grams of zirconium oxychloride ($ZrOCl_2.8H_2O$) were dissolved in 2 liters of distilled water. Separately, 55.6 grams of 85 vol % phosphoric acid (sp. gr. 1.70) were diluted with 1.9 liters of distilled water. The two solutions were then added dropwise to a reaction vessel held at a temperature of 40°C., at a constant rate over a period of about 3.4 hours using a constant amount delivery pump to carry out the reaction. In this case, the mole ratio $PO_4/Zr$ was 1.3 and the pH was below 1.0. After allowing the resulting gel-like white precipitate to stand 24 hours, the operation of adding 2 liters of water and filtering was repeated 5 times. When the pH became 3.4, separation by filtration was carried out, after which drying of the product was carried out for 24 hours at a temperature of 110°C. to obtain about 100 grams of a zirconium phosphate catalyst having a specific surface area of 325 $m^2$/gm. The measurement value for the foregoing specific surface area was obtained by the gas chromatographic method [The method proposed in F. M. Nelsen and F. T. Eggertsen, "Analytical Chemistry", vol. 30, No. 8, p. 1387 (1958). (The measurement of the specific surface areas in the subsequent examples was also made by this method.)].

EXAMPLE 2

Five hundred grams of $TiCl_4$ were dissolved in 2 liters of 1N-NCl. Separately, 395 grams of 85 vol % phosphoric acid were diluted with 1.9 liters of distilled water. This was followed by reacting the two solutions as in Example 1 and washing the precipitate 7 times with distilled water. The mole ratio $PO_4/Ti$ at the time of the preparation of the catalyst in this case was 1.3, and the pH was below 1.0. Further, the specific surface area of the resulting catalyst obtained was about 350 $m^2/gm$. On the other hand, the catalyst obtained by changing the mole ratio $PO_4/Ti$ to 2.0 (amount used of phosphoric acid 607 grams) and the pH to below 1.0 had a specific surface area of about 10 $m^2/gm$.

EXAMPLE 3

Two hundred and ten grams of stannous chloride ($SnCl_4.5H_2O$) were dissolved in 600 ml of distilled water. Separately, 187 grams of $NaH_2PO_4.2H_2O$ were dissolved in 1.2 liters of 1.2N–NaOH solution. The former was rapidly added to the latter with stirring, following which the resulting precipitate was filtered, washed with distilled water until the pH became 3.2 and thereafter dried at a temperature of 110°C. for 24 hours to obtain a tin phosphate catalyst. In this case the mole ratio $PO_4/Sn$ at the time of the catalyst preparation was about 2 and the pH was 2.0.

EXAMPLE 4

Twenty-four grams of 85 vol % $H_3PO_4$ and 12 grams of NaOH were dissolved in 500 ml of water. Separately, 41 grams of $HfOC_2.8H_2O$ were dissolved in 500 ml of distilled water. While stirring the former at room temperature, the latter was mixed therewith and reacted. The pH of the mixed solution was 5.0 and the mole ratio $PO_4/Hf$ was about 2. The precipitate was treated as in Example 1 and a hafnium phosphate catalyst having a specific surface area of 152 $m^2/gm$ was obtained.

EXAMPLE 5

One hundred and twenty grams of $ZrOCl_2.8H_2O$ were dissolved in 3 liters of 1N-HCl, to which was then added with stirring a solution in 2.7 liters of distilled water of 55.6 grams of 85 vol % $H_3PO_4$ to carry out the reaction. In this case, the mole ratio $PO_4/Zr$ at the time of the preparation of the catalyst was 1.3 and the pH was below 1.0. The resulting white gel-like precipitate was treated as in Example 1 to obtain about 100 grams of a zirconium phosphate catalyst whose specific surface area was 325 $m^2/gm$.

EXAMPLE 6

Sodium hydroxide (11.6 grams) were added to 500 ml of distilled water, to which were then added 24 grams of 85 vol % phosphoric acid and further a solution in 500 ml of distilled water of 32.2 grams of zirconium oxychloride, the addition being made with vigorous stirring. The pH at the time of catalyst preparation was 3.8 and the mole ratio $PO_4/Zr$ was 2.0. The resulting gel-like precipitate, after being allowed to stand for 24 hours, was separated by filtration, water-washed and dried at 110°C. The resulting phosphate was treated with 1N-HCl to convert it to an H type zirconium phosphate, after which it was calcined at 300°C. for one hour in a nitrogen stream to obtain a catalyst having a specific surface area of 306 $m^2/gm$.

EXAMPLE 7

Nineteen grams of $TiCl_4$ were dissolved in 500 ml of 1N-HCl. Separately, 24 grams of 85 vol % phosphoric acid were diluted with 500 ml of distilled water. After which the two solutions were mixed at room temperature with stirring. The formation of precipitate began with the mixing of the two solutions. Next, the pH of the solution was adjusted to 5.0 by gradually adding concentrated ammonia water, followed by allowing the solution to stand for 24 hours. The precipitate was then separated by filtration, water-washed and dried at 300°C. for one hour. The so obtained titanium phosphate had a specific surface area of 169 $m^2/gm$. The mole ratio $PO_4/Ti$ at the time of catalyst preparation was 2.0 in this case.

EXAMPLE 8

A solution in 5 liter of distilled water of 120 grams of $ZrOCl_2.8H_2O$ was added with thorough stirring to a solution in 5 liter of distilled water of 74 grams of 85 vol % phosphoric acid and 90 ml of of 28 % ammonia water (sp. gr. 0.9). The resulting white precipitate (the pH of the supernatant liquid 4.8) was separated by filtration and washed until the chlorine ions disappeared. The so obtained gel was dried at 80°C. for 14 hours, followed by comminuting to particle size of 16–48 mesh, calcining at 400°C. for 3 hours under a nitrogen atmosphere and complete elimination of the ammonia formed by decomposition to obtain about 100 grams of zirconium phosphate having a specific surface area of 184 $m^2/gm$. The mole ratio $PO_4/Zr$ at the time of catalyst preparation was 2.0 in this case.

EXAMPLE 9

An externally heated type 300-ml autoclave of a normal operating pressure of 50 $kg/cm^2$ was charged with 120 grams of acetone and 20 grams of the zirconium phosphate catalyst obtained in Example 1, and the condensation reaction was carried out under the reaction conditions indicated in Table I. After completion of the reaction, the autoclave was allowed to cool to room temperature, then cooled in ice water, after which the catalyst was separated by filtration, and the filtrate was analyzed by gas chromatography. The results obtained are shown in Table I. When the reaction temperature is relatively low, it is seen that mesityl oxide (hereinafter abbreviated to MO in all the subsequent examples) is principally formed, whereas as the temperature becomes higher, the formation of 1,3,5-trimethyl-benzene (hereinafter abbreviated to MB) increases. In order to render the results of Table I more clear and facilitate their understanding, the conversions of MO and MB as well as the overall conversion relative to the reaction temperature are shown graphically in FIG. 1.

Table I

| Experiment No. | Reaction Conditions | | | Results | | | |
|---|---|---|---|---|---|---|---|
| | Temperature (°C.) | Time (hr) | Max. pressure (kg/cm$^2$) | Conversion (%) | Selectivity (%) | | |
| | | | | | MO | MB | Others |
| 1 | 70 | 1 | 1.3 | 10.2 | 100 | — | — |
| 2 | 108 | 1 | 4.1 | 22.3 | 99.3 | 0.1 | 0.6 |
| 3 | 120 | 1 | 4.3 | 28.1 | 95.3 | 1.2 | 3.5 |
| 4 | 165 | 1 | 14.3 | 30.0 | 61.2 | 17.8 | 21.0 |
| 5 | 215 | 1 | 37.9 | 41.9 | 38.7 | 50.4 | 11.9 |

In the graph of FIG. 1, the curve a represents the overall conversion rate (%), whereas curve b represents the conversion (%) to mesityl oxide (MO), curve c, the conversion (%) to 1,3,5-trimethylbenzene (MB), and curved d, the conversion (%) to the other products.

EXAMPLE 10

Thirty ml of acetone and 10 grams of the zirconium phosphate catalyst obtained in Example 1 were placed in a round-bottomed 300-ml flask and refluxed for about 2 hours. After completion of the refluxing, the flask was cooled in ice water, and the catalyst was removed by decantation, after which the supernatant liquid was analyzed as in Example 9. As a result, the conversion of acetone was about 30 %, and the selectivity of MO and MB were respectively 80 % and 1 %.

EXAMPLE 11

Catalysts obtained by operating as in Example 1 but by varying the mole ratio PO$_4$/Zr variously were used and condensation reactions of acetone were carried out by operating as in Example 9 excepting that the reaction temperature was maintained at 140°C. The results obtained are shown in Table II.

Table II

| Experiment No. | Mole ratio PO$_4$/Zr at time of catalyst preparation | Specific surface area (m$^2$/gm) | Conversion (%) |
|---|---|---|---|
| 1 | 1.3 | 340 | 34 |
| 2 | 1.5 | 240 | 28 |
| 3 | 2.0 | 15 | 8 |
| 4 | 3.0 | little less than 15 | 11 |

EXAMPLE 12

Condensation reactions of acetone and methyl ethyl ketone (hereinafter abbreviated to MEK) were carried out as in Example 9 for one hour under the reaction conditions indicated in Table III, using the catalyst obtained as in Example 2. The results obtained are shown in Table III. In said Table III the mole ratio denotes the mole ratio PO$_4$/Ti at the time of catalyst preparation and the abbreviation MHO (equally applicable in the subsequent examples) denotes 3-methylheptene-5-one.

Table III

| Experiment No. | Reaction Condition | | | | Catalyst | | Results | | |
|---|---|---|---|---|---|---|---|---|---|
| | Class of ketone | Amount of catalyst (gm) | Reaction temperature (°C) | Maximum pressure (kg/cm$^2$) | Mole ratio (P/Ti) | Specific surface area (m$^2$/gm) | Conversion (%) | Selectivity (%) | |
| | | | | | | | | MO | MHO |
| 1 | acetone | 15 | 130 | 7.5 | 1.3 | 350 | 24 | 97 | — |
| 2 | acetone | 15 | 130 | 7.5 | 2.0 | 10 | 11 | 98 | — |
| *3 | MEK | 14 | 145 | 7.1 | 1.8 | 14 | 7.6 | — | 99.8 |

*The product of Experiment No. 3 is a mixture of isomers in which the position of double bond of MHO differs.

EXAMPLE 13

The condensation reaction of acetone was carried out as in Example 9 at a temperature of 130°C. for 1 hour, using 15 grams of the tin phosphate catalyst obtained in Example 3. The maximum pressure in this experiment was 7.6 kg/cm$^2$. As a result, the conversion of acetone was 7.9% and the selectivity of MO was 98.9%.

EXAMPLE 14

Eight ml of the zirconium phosphate catalyst obtained in Example 1 were first prepared into particle size of 30–60 mesh and packed into a stainless steel reaction tube 6 mm in inside diameter and 20 cm high. While maintaining the temperature inside the reaction tube at 260°C., acetone preheated in advance to 230°C. was introduced into the reaction tube at a space velocity of 0.875. With a reaction time of 2 hours MB was obtained at an average conversion of 47 % and selectivity of 62 %.

EXAMPLE 15

Fifteen ml of the zirconium phosphate catalyst obtained in Example 5 was packed into the middle part of a stainless steel reaction tube 28 mm in inside diameter and 400 mm high, after comminuting to particle size of 16–48 mesh. The results obtained by carrying out the condensation reactions by passing acetone through under varied conditions are shown in Table IV.

Table IV

| Experiment No. | Reaction Conditions | | | Results | | | | Average space yield of MO (g/l catalyst/hr) |
|---|---|---|---|---|---|---|---|---|
| | Reaction temperature (°C) | Reaction pressure (kg/cm$^2$) | Liquid hourly space velocity (hr$^{-1}$) | Acetone Conversion (%) | | MO Selectivity (mol %) | | |
| | | | | After passage of 4 hours | After passage of 50 hours | After passage of 4 hours | After passage of 50 hours | |
| 1 | 115 | 5.0 | 1.4 | 24.0 | 24.3 | 99.0 | 99.0 | 225 |
| 2 | 115 | 5.0 | 4.0 | 10.8 | 10.5 | 99.1 | 99.2 | 278 |
| 3 | 115 | 5.0 | 6.9 | 5.5 | 5.8 | 98.9 | 99.0 | 265 |
| 4 | 123 | 6.0 | 1.4 | 27.0 | 26.7 | 98.0 | 97.8 | 247 |

EXAMPLE 16

Condensation reactions of various classes of ketones were carried out, using 15 ml of the several catalysts obtained in Examples 2–5 packed in the middle part of the reaction tube used in Example 15. In Table V are shown the results obtained after the passage of 4 hours.

APH — acetophenone
EMHO — 3-ethyl-4-methylheptene-5-one
TMNO — 2,6,8-trimethyl nonenone-4
ONHO — 11-octyl-12-nonylheneicosenone-10
DCHB — 2,4-dicyclohexylbutenone-4
DPHB — 1,3-diphenyl-2-butene-1-one Table V

| Experiment No. | Class of ketone | Class | Example No. | Reaction temperature (°C) | Reaction pressure (kg/cm$^2$) | Liquid hourly space velocity (hr$^{-1}$) | Conversion (%) | Product Name | Selectivity (mol %) |
|---|---|---|---|---|---|---|---|---|---|
| 1 | acetone | titanium phosphate | 2 | 115 | 5.0 | 4.0 | 10.0 | MO | 98.0 |
| 2 | acetone | tin phosphate | 3 | 115 | 5.0 | 4.0 | 3.5 | MO | 98.0 |
| 3 | acetone | hafnium phosphate | 4 | 115 | 6.0 | 4.0 | 7.5 | MO | 96.5 |
| 4 | MEK | zirconium phosphate | 5 | 145 | 6.8 | 2.0 | 16.0 | MHO | 99.0 |
| 5 | MEK | titanium phosphate | 2 | 145 | 6.8 | 2.0 | 15.0 | MHO | 98.0 |
| 6 | MEK | tin phosphate | 3 | 145 | 6.8 | 2.0 | 5.2 | MHO | 98.0 |
| 7 | MEK | hafnium phosphate | 4 | 145 | 6.8 | 2.0 | 10.0 | MHO | 97.0 |
| 8 | DEK | zirconium phosphate | 5 | 105 | 2.2 | 4.0 | 5.5 | EMHO | 98.0 |
| 9 | MIBK | zirconium phosphate | 5 | 120 | 2.0 | 2.0 | 6.4 | TMNO | 97.5 |
| 10 | DNK | zirconium phosphate | 5 | 130 | 1.0 | 2.0 | 5.0 | ONHO | 87.0 |
| 11 | DNK | titanium phosphate | 2 | 130 | 1.0 | 2.0 | 4.6 | ONHO | 86.0 |
| 12 | DNK | tin phosphate | 3 | 130 | 1.0 | 2.0 | 1.8 | ONHO | 86.5 |
| 13 | DNK | hafnium phosphate | 4 | 130 | 1.0 | 2.0 | 3.5 | ONHO | 84.0 |
| 14 | MCK | zirconium phosphate | 5 | 130 | 1.0 | 2.0 | 5.3 | DCHB | 83.3 |
| 15 | APH | zircinium phosphate | 5 | 200 | 1.0 | 1.0 | 4.0 | DPHB | 80.0 |
| 16 | APH | titanium phosphate | 2 | 200 | 1.0 | 1.0 | 3.8 | DPHB | 80.0 |
| 17 | APH | tin phosphate | 3 | 200 | 1.0 | 1.0 | 1.4 | DPHB | 78.9 |
| 18 | APH | hafnium phosphate | 4 | 200 | 1.0 | 1.0 | 3.4 | DPHB | 75.3 |

NOTE: The abbreviations in Table V are those of the following compounds:
DEK — diethylketone
MIBK — methylisobutylketone
DNK — dinonylketone
MCK — methylcyclohexylketone

EXAMPLE 17

Condensation reactions of acetone were carried out by packing 15 ml of the several catalysts obtained in Examples 6–8 into the middle part of the reaction tube used in Example 15. The results obtained after passage of 50 hours are shown in Table VI. Practically no trimeric condensation products were noted.

Table VI

| Experiment No. | Reaction conditions ||| Results ||||Catalyst used |
|---|---|---|---|---|---|---|---|---|
| | Reaction temperature (°C) | Reaction pressure (kg/cm²) | Liquid hourly space velocity (hr⁻¹) | Conversion (%) || MO selectivity (mol %) || |
| | | | | After passage of 2 hours | After passage of 50 hours | After passage of 2 hours | After passage of 50 hours | |
| 1 | 115 | 5.0 | 4.0 | — | 11.0 | — | 99.0 | Example 6 |
| 2 | 115 | 5.0 | 4.0 | — | 17.5 | — | 98.8 | Example 7 |
| *3 | 115 | 5.0 | 4.0 | 20.6 | 21.0 | 99.0 | 99.0 | Example 8 |

*The average space yield of the MO of Experiment No. 3 was 577 g/l catalyst/hr.

EXAMPLE 18

Four ml of the zirconium phosphate catalyst obtained in Example 1 was packed into a Pyrex reaction tube 12 mm in inside diameter and 40 cm high, following which a mixture (mole ratio = 1:1) of acetone and methyl ethyl ketone was introduced thereinto at the rate of 1.7 ml/hr while maintaining the reaction temperature at 170°C. The resulting reaction product had the composition shown in Table VII.

Table VII

| Name of substance | Composition (mol %) |
|---|---|
| acetone | 19.5 |
| methyl ethyl ketone | 28.5 |
| mesityl oxide | 11.1 |
| 2-methyl-hexene-4-one | 10.3 |
| 3-methyl-hexene-5-one | 5.3 |
| 3-methyl-butene-5-one | 3.3 |
| diisobutenylketone | 9.9 |
| 2-methyl-4-ethyl-heptene-6-one | 6.7 |
| 2,6,8-trimethylnonenone | 2.3 |
| Others | 3.1 |

EXAMPLE 19

An externally heated type 300-ml autoclave was charged with 100 grams of a 9:1 molar mixture of diphenylketone and acetone and 20 grams of the zirconium phosphate catalyst obtained in Example 1, after which the reaction was carried out at 200°C. for 2 hours at a maximum pressure of 35 kg/cm². As a result, the composition of the product obtained was as shown in Table VIII.

Table VIII

| Name of substance | Composition (mol %) |
|---|---|
| diphenylketone | 90.0 |

Table VIII-continued

| Name of substance | Composition (mol %) |
|---|---|
| acetone | 1.0 |
| 1,1-diphenylbutene 3-one | 2.0 |
| mesityl oxide | 4.0 |
| 1,3,5-trimethyl-benzene | 3.0 |

We claim:

1. A process of producing unsaturated ketone condensation products which comprises condensing at a temperature of from 60° to 300°C., a ketone of 3–19 carbon atoms having the following formula

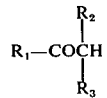

wherein $R_1$ is either alkyl, cycloalkyl, aryl, aralkyl, alkaryl or alkenyl, and $R_2$ and $R_3$, which may be the same or different are each hydrogen, alkyl, cycloalkyl, aryl, aralkyl, alkaryl or alkenyl, said process being carried out in the presence of a catalyst consisting of at least one metal phosphate selected from the group consisting of titanium phosphate, zirconium phosphate, hafnium phosphate, and tin phosphate.

2. The method of claim 1 wherein dimeric condensation products are selectively formed by carrying out the condensation reaction at a temperature of 60° to 160°C.

3. The method of claim 1 wherein dimeric condensation products are selectively produced by carrying out the condensation reaction in the liquid phase.

4. The method of claim 1 wherein said ketone is selected from the group consisting of acetone, diethylketone, methyl ethyl ketone, methylisobutylketone, and mixtures thereof.

* * * * *